United States Patent

Bierman et al.

[11] Patent Number: 5,192,273
[45] Date of Patent: Mar. 9, 1993

[54] CATHETERIZATION SYSTEM

[75] Inventors: Steven F. Bierman, 143 Eight St., Del Mar, Calif. 92014; David C. Howson, Denver, Colo.

[73] Assignee: Steven F. Bierman, Del Mar, Calif.

[21] Appl. No.: 518,964

[22] Filed: May 4, 1990

Related U.S. Application Data

[63] Continuation-in-part of Ser. No. 384,326, Jul. 24, 1989, abandoned.

[51] Int. Cl.$^5$ .............................................. A61M 5/32
[52] U.S. Cl. ..................................... 604/174; 604/905
[58] Field of Search ............... 604/180, 179, 178, 177, 604/174, 905; 128/DIG. 26

[56]        References Cited

U.S. PATENT DOCUMENTS

| | | |
|---|---|---|
| 747,360 | 12/1903 | Barry . |
| 2,525,398 | 10/1950 | Collins . |
| 2,533,961 | 12/1950 | Rouseau et al. . |
| 3,064,648 | 11/1962 | Bujan . |
| 3,167,072 | 1/1965 | Stone et al. ................. 604/179 |
| 3,394,954 | 7/1968 | Sarns . |
| 3,686,896 | 8/1972 | Rutter . |
| 3,766,915 | 10/1973 | Rychlik . |
| 3,856,020 | 12/1974 | Kovac ..................... 604/177 X |
| 3,900,026 | 8/1975 | Wagner . |
| 3,906,946 | 9/1975 | Nordstrom . |
| 3,920,001 | 11/1975 | Edwards . |
| 3,973,565 | 8/1976 | Steer . |
| 4,037,599 | 7/1977 | Raulerson . |
| 4,082,094 | 4/1978 | Dailey . |
| 4,084,911 | 4/1978 | DeWitt . |
| 4,099,744 | 7/1978 | Kutnyak et al. . |
| 4,114,618 | 9/1978 | Vargas . |
| 4,116,196 | 9/1978 | Kaplan et al. . |
| 4,123,091 | 10/1978 | Cosentino et al. . |
| 4,129,128 | 12/1978 | McFarlane . |
| 4,133,312 | 1/1979 | Burd . |
| 4,161,177 | 7/1979 | Fuchs . |
| 4,224,937 | 9/1980 | Gordon . |
| 4,250,880 | 2/1981 | Gordon ...................... 604/180 |
| 4,316,461 | 2/1982 | Marais et al. . |
| 4,326,519 | 4/1982 | D'Alo et al. . |
| 4,362,156 | 12/1982 | Feller, Jr. et al. . |
| 4,392,853 | 7/1983 | Muto . |
| 4,405,163 | 9/1983 | Voges et al. ............. 604/905 X |
| 4,449,975 | 5/1984 | Perry . |
| 4,474,559 | 10/1984 | Steiger . |
| 4,516,968 | 5/1985 | Marshall et al. . |
| 4,585,435 | 4/1986 | Vaillancourt . |
| 4,711,636 | 12/1987 | Bierman .................... 604/180 |
| 4,752,292 | 6/1988 | Lopez et al. . |
| 4,792,163 | 12/1988 | Kulle .................... 604/905 X |
| 4,838,858 | 6/1989 | Wortham et al. . |
| 4,863,432 | 9/1989 | Kvalo . |
| 4,880,412 | 11/1989 | Weiss . |
| 4,966,582 | 10/1990 | Sit et al. . |
| 4,981,469 | 1/1991 | Whitehouse et al. . |
| 4,997,421 | 3/1991 | Palsrok et al. . |

FOREIGN PATENT DOCUMENTS

| | | |
|---|---|---|
| 2341297 | 4/1975 | European Pat. Off. . |
| 114677 | 8/1984 | European Pat. Off. . |
| 169704 | 1/1986 | European Pat. Off. . |
| 0263789 | 9/1986 | Fed. Rep. of Germany . |
| 2063679 | 6/1981 | United Kingdom . |

Primary Examiner—John J. Wilson
Assistant Examiner—Jeffrey A. Smith
Attorney, Agent, or Firm—Knobbe, Martens, Olson & Bear

[57]        ABSTRACT

A tubular adaptor releasably interconnects an IV conventional catheter hub to fluid supply tubing. A latching clip slidably mounted on the adaptor cooperates with flange portions on the catheter hub to secure the interconnection between the hub and the adaptor. The adaptor is snapped into a base attached to the patient's skin by an adhesive pad. After the catheter connection is made, the adaptor, together with the clip, is rotated about 90° on the base into a low profile position, wherein the clip is close to the patient's skin.

14 Claims, 3 Drawing Sheets

CATHETERIZATION SYSTEM

This is a continuation-in-part of co-pending U.S. patent application No. 384,326, filed Jul. 24, 1989, now abandoned.

BACKGROUND OF THE INVENTION

The present invention relates to a percutaneous catheterization system, and, more particularly, to a system which facilitates the frequent replacement of the catheter tubing which is necessary in such catheterization procedures.

It is very common in the treatment of hospitalized patients to utilize intravenous (IV) catheters to introduce certain fluids directly into the bloodstream of the patient. Such procedures are also becoming more common outside of the hospital as the high cost of hospital medical care has brought about the advent of neighborhood out-patient clinics and home health care.

In IV catheterization, a supply of fluid is maintained in a container which is located at a height higher than the patient. The catheter tubing flows from the supply container to the location of introduction into the patient where it is attached to a catheter. This location is typically the back of the patient's hand or a vessel on the inside of the arm. Typically, a needle or other stylet is first introduced through the cannula portion of the catheter and into the skin of the patient at the desired location, and then removed after the cannula is inserted into the skin. The fluid then flows directly into the blood vessel of the patient by gravity, or, if necessary, by the pressure generated by the head of the fluid above the height of the patient.

In common practice, the catheter is maintained in place on the skin of the patient by the use of adhesive or surgical tape. Likewise, the connection between the tubing and the catheter is also maintained by use of tape. In addition, a safety loop is typically formed in the tubing so that any tension applied to the tubing is not passed directly to the cannula of the catheter but is taken up in the slack of the safety loop. This loop is also typically taped loosely to the skin of the patient. This entire taping procedure takes several minutes of the valuable time of health practitioners performing this procedure.

IV catheterization is frequently maintained for several days, depending upon the condition of the patient. This longevity requirement gives rise to several problems associated with IV catheters. For example, the catheter tubing is generally replaced every 24 to 48 hours in order to maintain the sterility of the fluid and the free-flow of the fluid through the tubing. Thus, a health practitioner is often called upon to frequently change the tubing and to retape the connection. Furthermore, the taping of the catheter to the skin of the patient often covers the location of insertion of the cannula. Thus, the tape must be removed in order to inspect the insertion location for inflammation or infection and a complete taping procedure again be initiated. In short, a great deal of valuable time of the health practitioner is used in applying significant amounts of surgical tape to IV catheters. Further, the frequent application and removal of surgical tape often results in the excoriation of the skin of the patient in the area of the insertion.

A number of catheterization systems have recently been developed which improve the stabilization of the catheter system and/or obviate the need for frequent application and removal of surgical tape during IV tubing changes. One such system is shown in U.S. Pat. No. 4,250,880, wherein a disposable catheter stabilizing fitting comprising a catheter hub-retaining cradle is attached to a laminar base, the base having an adhesive undersurface for attachment to the patient. The cradle is designed to hold the catheter hub at a suitable angle to avoid bending or crimping of the catheter so as to facilitate access to the point of catheter insertion to the skin, however, the device is still required to be secured and stabilized by being overlaid with adhesive tape.

Another catheterization system is described in U.S. Pat. No. 4,711,636, comprising a specially designed cannula which is attachable via an adaptor to an IV tubing. The cannula is removably attached to a base, which is adhesively attachable to the skin of a patient. The cannula is adapted to be secured to the base portion in a snap-fit engagement so as to obviate the necessity for the time consuming application of surgical tape or other apparatus to stabilize the catheter, as previously mentioned. However, this cannula is specially adapted for attachment to the base portion of the assembly, and therefore, cannot be used with conventional luer-type connectors on conventional cannula apparatus.

The above-referenced pending parent patent application discloses a system which represents an improvement over the apparatus shown in above-mentioned U.S. Pat. No. 4,711,636 in that the system in the pending application can be used with conventional luer-type connectors on conventional cannula apparatus. However, one of the difficulties of utilizing an adaptor which can attach to conventional connectors is that there are some dimensional variances in conventional connectors. Typically, such connectors employ a tapered hub with an outwardly extending flange on the larger end. That pending application employs a retention latch which is manually movable to latch onto the flange on the end of the connector, and thus securely hold the connector with respect to the adaptor. This works quite well with most standard-type connectors, but connectors having slight dimensional variations do not fit so well because there is no means in the latch to accommodate such variations. Thus, a need exists for a latch that can handle such variations.

The manually operated mechanism for opening the latch in the above-referenced application and in the above-mentioned U.S. Pat. No. 4,711,636 extends outwardly away from the patient skin to facilitate operation. While the device is relatively small, it does extend outwardly enough such that it can interfere in taping or other medical procedures, or can interfere with patient movement. Thus it is desirable that a system be provided which improves that aspect.

SUMMARY OF THE INVENTION

Briefly stated, the invention employs an adaptor having a tubular portion with a forward end adapted to be inserted within the end of a standard luer-type connector; and a clip slidably mounted on the adaptor to latch the connector to the adaptor. The clip includes a forward latch portion which cooperates with a flange on the rear of the connector to secure the connector to the adaptor. Because the clip is slidable, it can accommodate variations in the axial position of the connector flange. Preferably, the latch has a somewhat flexible forked tip that straddles the end of the connector, and accommodates variations in connector diameters.

In a preferred form of the invention, the clip is mounted on the adaptor by means of an elongated plate-like ratchet element which extends parallel to the adaptor tubular portion. The element is mounted on the end of an arm that extends radially outwardly from the adaptor tubular portion. The clip is slidably mounted on this plate-like ratchet element. Depressing the rear of this element, with the clip mounted thereon, toward the adaptor tubular portion allows it to pivot about the arm so as to move the forward end of the ratchet element, together with the forked end of the clip, radially outwardly to permit engagement and disengagement of the connector to the end of the adaptor. Withdrawing the depressing force allows the forked end of the clip to return inwardly to its normal latching position.

The clip and the ratchet element include interengaging ratchet teeth and an interengaging pawl for maintaining those parts in a manually selected position. In a preferred form of the invention, the ratchet teeth are formed on the radially outer surface of the ratchet element and a tongue-like, resiliently mounted pawl formed on the clip cooperates with these teeth.

The apparatus also includes a base which is adapted to be attached to the patient's skin. The base has a pair of upstanding legs which define a space for receiving the adaptor and are constructed to flex outwardly at the upper end to provide a snap fit with the adaptor. Preferably, this snap fit includes an inwardly extending detent on the upper end of each leg. The detents fit within an annular groove formed on the outer surface of the adaptor tubular portion. The detents hold the adaptor to the base and permit the adaptor to rotate from its upright position, when the connection is being made to the connector on the end of a catheter, into a lower profile "stored" position closer to the base and the patient's skin. In this position the components are less likely to interfere with other surrounding actions.

DETAILED DESCRIPTION OF A PREFERRED EMBODIMENT

Figure 1:
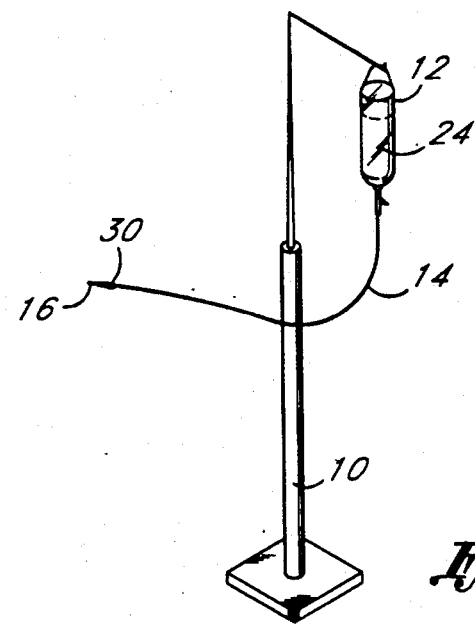
FIG. 1 is a perspective, schematic view of a typical catheterization installation using the catheter adaptor of the present invention.

Referring now to FIG. 1 there is shown a basic set-up for a catheterization procedure, including a support stand 10, a container 12, a length of IV tubing 14 connected by an adaptor 30 to the actual catheter 16, which is inserted into the patient. Typically, a patient is lying in a bed or is seated adjacent to a stand 10. Fluid 24, to be dispensed into the patient, is maintained in the container 12 and is fed under the pressure of the head of the fluid above the patient, through the IV tubing 14 and catheter 16 into the patient.

Figure 2:
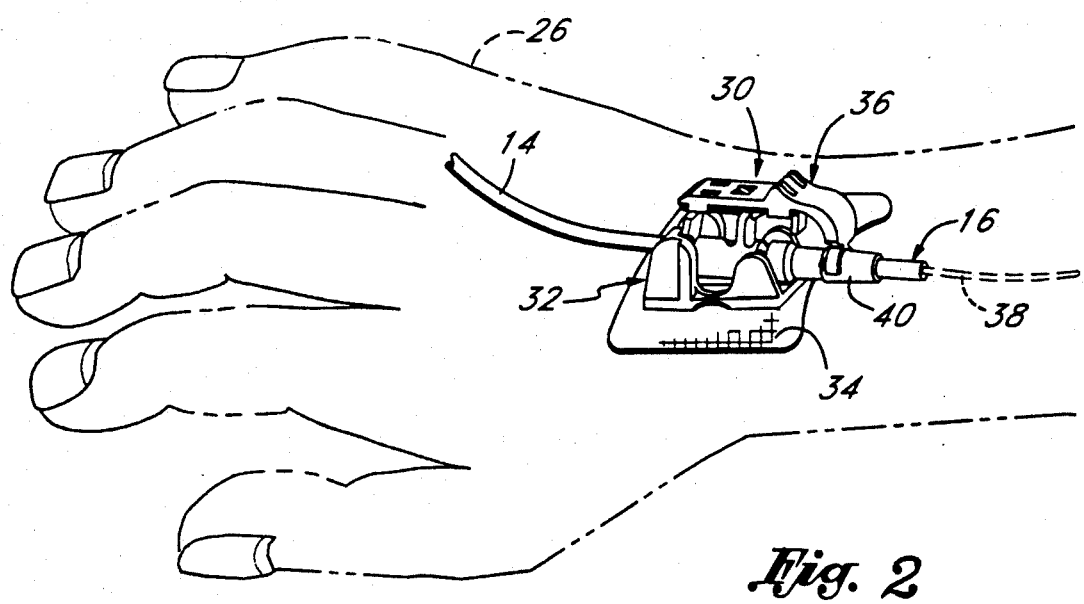
FIG. 2 is a perspective view of catheterization apparatus of the present invention, mounted on the back of a patient's hand.
Figure 3:
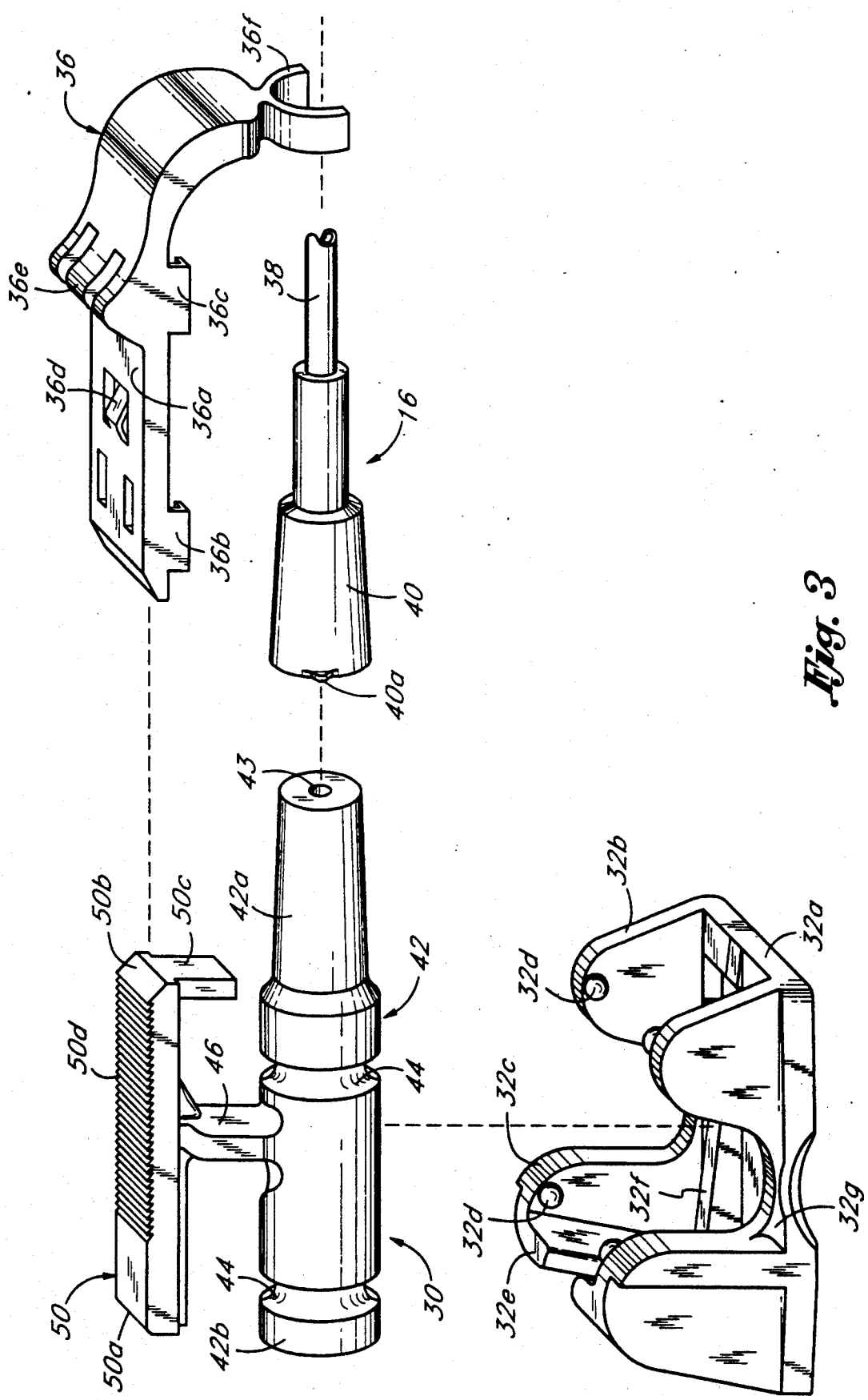
FIG. 3 is an exploded perspective view of the apparatus of FIG. 2.

FIG. 2 illustrates an enlargement of the catheterization apparatus of the present invention, positioned in the back of a patient's hand 26, shown in phantom lines. As better seen in FIGS. 3 and 4, the apparatus includes the adaptor 30 interconnecting the catheter 16 and the tubing 14, a base support 32 mounted on a pad 34, and a latching clip 36. The catheter 16 includes a cannula 38 and a conventional hub 40, having a frustoconical shape and terminating at its rear end in radially outwardly extending flange portions 40a. Some hubs have a continuous flange.

The adaptor 30 includes a main elongated tubular body 42 having a passage 43 therethrough. The body has a forward end 42a which tapers to fit within an opening in the catheter hub 40. The rear end 42b of the tubular body 42 is adapted to receive the downstream end of the tubing 14. The adaptor further includes a pair of axially spaced annular grooves 44 formed on the exterior of the tubular body. Extending outwardly from the body 42 in cantilever fashion is a support arm 46. Positioned on the radially outer end of the arm 46 is a ratchet element 50 that extends generally parallel to and spaced from the axis of the tubular body 42. The connection to the support arm 46 is between the ends of the ratchet element 50. The adaptor body 42, the arm 46 and the ratchet element 50 are preferably formed as one piece, preferably of a stiff but somewhat flexible plastic. Thus, although the arm 46 and the element 50 are stiff, the element can pivot somewhat about the upper end of the arm, and the arm can flex somewhat about its lower end. Thus depressing the rear end 50a of the ratchet element 50 towards the body 42, will correspondingly move the forward end 50b away from the body 42.

Formed integral with the forward end 50b is a depending stop 50c, which extends toward the body 42 and limits the movement of the forward end 50b towards the tubular body, and prevents fatigue of flexing of the arm 46 and element 50. Formed on the upper or radially outer, flat surface of the ratchet element 50 are a series of ratchet teeth 50d which extend laterally generally parallel to the axis of the tubular body.

The anchor pad 34 is preferably made of a woven cloth material having a self-adhesive backing for attachment to the skin; or alternatively, a foam material with adhesive back. The anchor pad may also be connected to a support for a loop of tubing, and the pad may be specially formed for a left hand or a right hand mounting.

The adaptor base 32 has a generally rectangular lower wall 32a, having its lower surface suitably attached to the top surface of the anchor pad. A pair of spaced upstanding legs 32b are located on the forward end of the base, and a second pair of outwardly extending legs 32c are mounted on the rear portion of the lower wall 32a. These legs define a space sized to receive the tubular body of the adaptor 30. Each leg has on its upper end an inwardly extending detent or nib 32d. The spacing between detents in each pair of legs is slightly less than the smaller diameter of the grooves 44 on the adaptor. Also, the detents 32d on the legs 32b are spaced upwardly from the bottom wall 32a a distance greater than the radius of the adaptor tubular body, and the detents 32d on the legs 32c are spaced above a rib 32f.

The base is made of relatively stiff plastic material but is somewhat flexible, such that the upper ends of the legs, which are supported in cantilever fashion from the base wall 32, can be forced outwardly by the adaptor when it is placed between the legs. When the adaptor is seated, the upper ends of the legs snap inwardly to their original position, such that the adaptor is securely held within the base. Since the detents 32d are positioned within the annular grooves 44, the adaptor is also securely positioned in its axial direction. The base also includes a rear upstanding wall 32e, which further helps position the adaptor within the base. The base rib 32f is positioned between the legs 32c and extends upwardly to support the adaptor. The upper edge of the rib is angled so that it is higher towards the rear of the base than it is towards the forward portion, with the result that the adaptor is positioned at a desired angle. A horizontal ledge 32h (FIG. 4) can be provided on the interior side of the rear wall 32f at the rib height to further support the adaptor.

The base 32 includes a waist area 32g on the bottom wall 32a between the front and rear legs. This area extends inwardly from the sides of wall 32a and slightly beneath the adaptor to facilitate gripping the adaptor with a thumb and forefinger.

The clip 36 has a main portion 36a with a generally flat rectangular shape. The clip has positioned on its side edges a forward pair of depending, retainer lugs 36c and a rear pair of depending retainer lugs 36b. These lugs include inwardly extending portions which in cooperation with the lower surface of the main portion 36a define side spaces to receive the ratchet element 50 on the adaptor.

Figure 4:
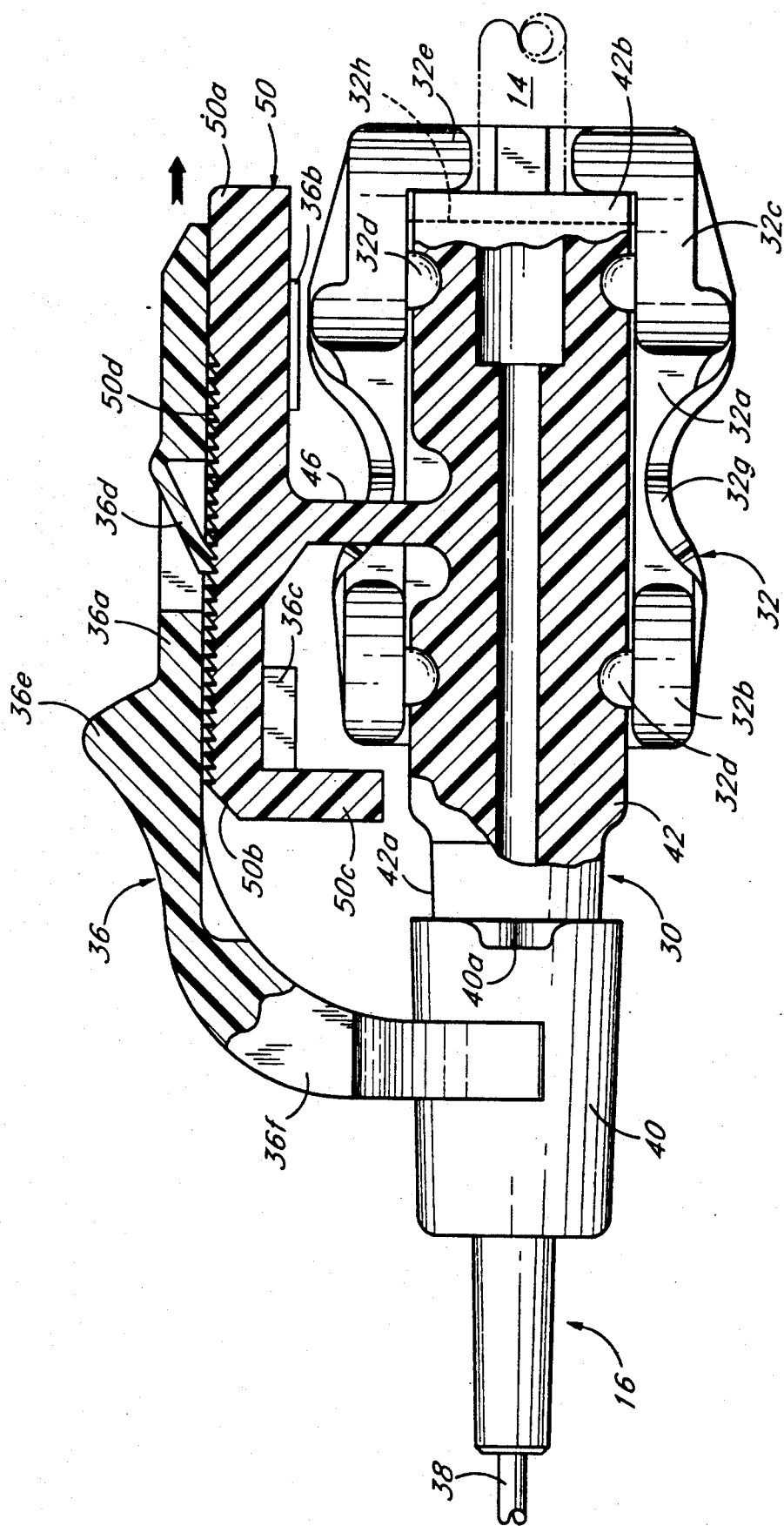
FIG. 4 is a plan, partially sectionalized view of the apparatus of FIG. 3, illustrating the operation of the resiliently-mounted movable clip and ratchet arrangement.

Centrally positioned in the clip is a tongue or pawl 36d supported in cantilever fashion from the main body 36a of the clip. The rear portion of the pawl is formed integral with the body 36a, and the forward end is free and depends downwardly below the lower surface of the body as best seen in FIG. 4. The lower edge of the pawl is a straight line and is adapted to cooperate with the ratchet teeth 50d on the ratchet element 50 of the adaptor.

Positioned slightly forwardly from the tongue is an upwardly extending bump 36e adapted to be engaged by a person's finger or thumb so as to slide the clip 36 on the ratchet element 50. The forward end of the clip curves downwardly and includes a fork-shaped latch 36f adapted to straddle the hub of the catheter. The latch preferably has a curved circular shape that extends more than 180°, such as 190° to 200°. This horseshoe shape enables the latch to slip onto a tapered hub but yet lightly grip it and enables the latch to accommodate a variety of hub shapes and surfaces.

In use, the catheter 16 is installed in conventional fashion. That is, a needle is inserted into the patient's blood vessel; and while holding the needle still, the conventional catheter 16 is slid over the needle and into position within the vessel. The needle is then carefully withdrawn leaving the catheter in position. The forward end 42a of the adaptor 30 is inserted into the catheter hub 40. In accordance with the invention, the clip 36 which has been slidably mounted on the adaptor ratchet element 50 is in a forward position so that it does not interfere with the insertion of the adaptor into the catheter hub. The 36 is then slid rearwardly causing its forked latch 36f to engage the forward surface of the flange portion 40a on the catheter hub, thereby securely attaching the adaptor to the catheter.

Because conventional catheter hubs have dimensional variations, it is desirable that the clip be adjustable to accommodate the various sizes and yet securely hold the adaptor and the catheter hub together. The clip 36 is easily movable rearwardly on the ratchet element, and the ratchet teeth cooperate with the clip tongue to resist forward movement and hold the clip in the manually selected position.

The adaptor is then snapped into the base 32. In doing this, the adaptor is pressed between the upstanding legs of the base with the detents on the adaptor legs sliding within the annular groove to hold the adaptor in the base. The anchor pad 34 attached to the adaptor base is then positioned in the desired location adjacent to the puncture point in the patient's skin. As noted above, the adaptor and the upper end of the centrally located rib 32f and the ledge 32h in the base causes the forward end of the adaptor to be angled downwardly to be best aligned with the axis of the catheter hub.

To reduce the profile of the clip and the adaptor mounting arm, the adaptor together with the clip can be rotated about 90°, in either direction, to the low profile "stored" position shown in FIG. 4. In this position, the adaptor mounting arm extends between the front base legs 32b and the rear base legs 32c, such that the arm is close to the adaptor base, generally parallel to the patient's skin. The height of the assembly has been reduced to the height of the base 33 and thereby reducing the risk of the assembly interfering with surrounding actions. Once so positioned, the adaptor will normally remain in this position until the adaptor and its associated tubing is to be removed and replaced by another one.

In replacing an adaptor and tubing, the procedure is essentially reversed from that set forth above, except that the catheter remains in the patient and the adaptor base remains as positioned. Leaving the catheter in position, of course, minimizes discomfort to the patient, and allowing the adaptor base to remain eliminates irritation to the patient's skin that would be caused by removal and replacement. Also operator time is thus saved during such replacement. In removing the adaptor from the base, the attendant's forefingers and thumb can be placed in the base waist area, also engaging the adaptor. The adaptor is then snapped out of the base with a pinching action. The adaptor is separated from the catheter by depressing the rear of the clip and the clip support element to raise the latch so that the adaptor can be withdrawn rearwardly from the catheter.

While a preferred arrangement of the catheter mounting apparatus has been illustrated and described, it should be understood that various changes and modifications to the apparatus will readily come to mind and fall within the scope of the invention as set forth in the appended claims.

We claim:

1. An apparatus for removably connecting together a fluid supply tube and an intravenous catheter, said apparatus comprising:

an adaptor having a tubular body defined between a forward end and a rear end, said forward end being configured to engage a hub of the catheter and said rear end being configured to receive an end of the fluid supply tube, said adaptor body for defining a longitudinal axis;

a support arm cantilevered radially outwardly from said adaptor;

a clip support element mounted on said support arm, said clip support element having an elongated parallelepiped shape extending generally parallel to said longitudinal axis, said clip support element being mounted on an outer end of said support arm at a central section of said clip support element, the connection between said support arm, said adaptor body and said clip support element permitting pivoting movement of said clip support element about said adaptor body such that depressing a rear end of said clip support element toward said adaptor body moves a forward end of said clip support element away from said adaptor body;

a clip comprising a forward latch configured to engage the hub, said clip slidably connecting with said support arm to move in a direction parallel to said longitudinal axis of said adaptor, said clip pivotably connecting to said adaptor to move said forward latch radially outwardly away from said forward end of said adaptor; and an interengaging element maintaining said clip from sliding towards said froward end of said adapter, said interengaging element comprising ratchet teeth and a pawl which engages said teeth to prevent said latch of said clip from sliding towards said forward end of said adaptor.

2. The apparatus of claim 1, wherein said clip support element comprises a depending stop formed on the forward end of said clip support element, the stop being located to limit the movement of the forward end of said clip support element towards said tubular body.

3. The apparatus of claim 1, including a base adapted to be mounted on a patient and being adapted to support said adaptor, said base and said adaptor having structure providing a releasable snap-fit engagement that permits said adaptor to be moved about an axis through said body from an operative position wherein said support arm extends outwardly on a side remote from said base to a stored position wherein said support arm is located close to said base.

4. The apparatus of claim 3, wherein said base includes a pair of upwardly extending legs which are spaced to define a space for receiving said adaptor body, said legs each having a detent on an upper end which extends inwardly into said space, said adaptor body having a groove on its exterior which is adapted to receive said detents, the spacing and location of said detents in relation to the diameter of said groove being such that the tubular body may be manually pressed into said space and said detents cooperate with said groove to hold the tubular body in position on said base.

5. The apparatus of claim 1, wherein said teeth of said interengaging element are positioned on said clip support element and said pawl of said interengaging element extends from said clip and is flexibly biased against said teeth.

6. The apparatus of claim 1, wherein said clip support element has a pair of longitudinally extending side edges, and said clip comprises a plurality of lugs which engage said side edges of said clip support element to guide the movement of said clip on said clip support element.

7. An apparatus for supporting and facilitating the changing of tubing connected to a catheter, said apparatus comprising:

an adaptor having a tubular body with a forward end configured to connect to a hub of a catheter, and a rear end configured to connect to a tubing; and a base for mounting on a patient's skin, said base having a pair of upstanding legs spaced to define a space for receiving said adaptor body, said base legs having detents which fit within an annular groove on said tubular body in a manner permitting rotation of said adaptor about a longitudinal axis of said adaptor tubular body while remaining captured on said base.

8. The apparatus of claim 7, wherein said detents are formed on the upper end of each of said base legs and extend inwardly into said space defined between said base legs, said detents being spaced apart by a distance slightly less than a diameter of said annular groove and being located such that the adaptor snaps into said space with said detents extending into said annular groove, said detents holding said adaptor on said base and permitting said adaptor to be rotated with respect to the base.

9. The apparatus of claim 7, wherein said base includes a bottom wall, and said legs extend upwardly from the bottom wall, said base further includes a second pair of spaced upstanding legs spaced from the first mentioned pair of legs, and said adaptor includes a support arm attached to and extending generally radially outwardly from said body, said adaptor being rotatable from an upright position wherein said support arm extends upwardly away from said base bottom wall and generally parallel to said legs to a low profile position, wherein said support arm extends between said pairs of legs adjacent to said bottom wall.

10. The apparatus of claim 7, wherein said base comprises a bottom wall and means for supporting said adaptor body so that the rear end of the tubular body is positioned further away from said bottom wall than the forward end of said tubular body, said means being positioned between said base legs.

11. The apparatus of claim 10, wherein said means for supporting said adaptor body comprises an upwardly extending rib having a sloping upper surface which engages the adaptor body.

12. The apparatus of claim 7, wherein said adaptor additionally comprises:

a support arm cantilevered radially outwardly from said adaptor;

a clip comprising a forward latch configured to engage said hub, said clip slidably connecting with said support arm to move in a direction parallel to a longitudinal axis of said adaptor, said clip pivotably connecting to said adaptor to move said forward.latch radially outwardly away from said forward end of said adaptor; and an interengaging element maintaining said clip from sliding towards said forward end of said adaptor.

13. A method of connecting a tubing to a catheter, said method comprising the steps of:

inserting a forward end of an adaptor into a rear end of a catheter hub;

engaging said hub with a clip which is slidably mounted on said adaptor;

sliding said hub rearwardly on said adaptor to grip the catheter hub in a gripping position;

locking said clip to maintain said clip in said gripping position by means of interengaging structure on said clip and said adaptor;

mounting said adaptor body in a base;

attaching said base to a patient's skin; and rotating the adaptor body from a position in which said clip is positioned away from said patient's skin in a high profile position to a low profile position in which the clip is positioned close to the patient's skin.

14. A method of connecting a catheter to a supply tubing, said method comprising the steps of:

connecting a forward end of a tubular adaptor to a rear of a catheter hub with the rear of the tubular adaptor being connected to a supply tubing;

latching the adaptor to the catheter by means of movable latching structure positioned radially outwardly from one side of the tubular adaptor;
positioning said adaptor into a base attachable to a patient's skin; and
rotating the adaptor within said base from a high profile position in which said latching structure extends upwardly to a low profile position in which said latching structure lies adjacent to the patient's skin.

* * * * *

UNITED STATES PATENT AND TRADEMARK OFFICE
CERTIFICATE OF CORRECTION

PATENT NO. : 5,192,273
DATED : March 9, 1993
INVENTOR(S) : Bierman et al

It is certified that error appears in the above-indentified patent and that said Letters Patent is hereby corrected as shown below:

COlumn 6, line 56, change "for defining" to --body defining --.
Column 8, line 53, change "said hub" to --said clip --.

Signed and Sealed this

Twenty-eighth Day of December, 1993

Attest:

BRUCE LEHMAN

Attesting Officer    Commissioner of Patents and Trademarks